United States Patent [19]

Netzer et al.

[11] Patent Number: 4,576,615
[45] Date of Patent: Mar. 18, 1986

[54] CARBON DIOXIDE HYDROCARBONS SEPARATION PROCESS

[75] Inventors: David Netzer; Robert R. Huebel, both of Houston, Tex.

[73] Assignee: The Randall Corporation, Houston, Tex.

[21] Appl. No.: 642,308

[22] Filed: Aug. 20, 1984

[51] Int. Cl.$^4$ .............................................. B01D 53/14
[52] U.S. Cl. ............................................ 55/43; 55/48; 55/51; 55/68; 55/73
[58] Field of Search ............... 55/46, 68, 73, 48, 51, 55/40, 41, 42, 43

[56] References Cited

U.S. PATENT DOCUMENTS

| | | | |
|---|---|---|---|
| 3,453,835 | 7/1969 | Hochgesand | 55/68 |
| 3,710,546 | 1/1973 | Myumewald et al. | 55/73 X |
| 3,910,777 | 10/1975 | Jakob | 55/73 X |
| 3,935,188 | 1/1976 | Karwat | 55/68 X |
| 4,332,596 | 6/1982 | Ranke et al. | 55/73 X |
| 4,372,925 | 2/1983 | Cornelisse | 55/73 X |
| 4,462,814 | 7/1984 | Holmes et al. | 55/68 X |

*Primary Examiner*—Charles Hart
*Attorney, Agent, or Firm*—Richard H. Berneike

[57] ABSTRACT

Carbon dioxide is separated from light hydrocarbons such as methane and ethane by absorbing $CO_2$ gas with water at a pressure of at least 500 psia thus avoiding the $CO_2$—$C_2H_6$ azeotrope problem. The $CO_2$ is recovered from the absorbing water by pressure reduction and flashing and/or by heating and flashing. The process is particularly applicable to the recovery of high pressure pure carbon dioxide from the wellhead products of carbon dioxide flooding used in enhanced oil recovery. The high pressure pure carbon dioxide is liquified and reinjected to the well at the desired pressure.

7 Claims, 1 Drawing Figure

U.S. Patent  Mar. 18, 1986  4,576,615
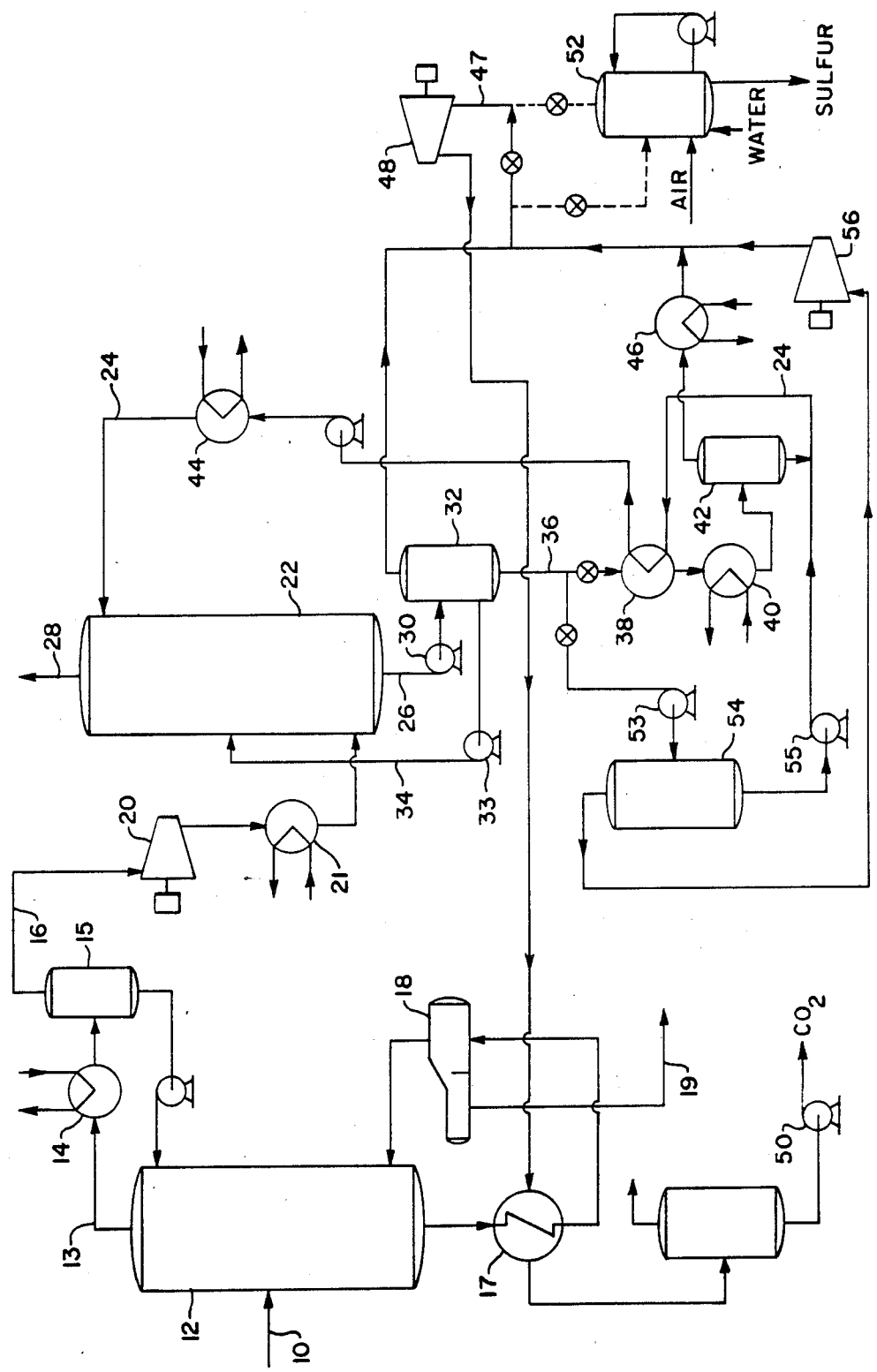

CARBON DIOXIDE HYDROCARBONS SEPARATION PROCESS

BACKGROUND OF THE INVENTION

The present invention relates to the absorption of $CO_2$ from light hydrocarbons at partial pressures in excess of 120 psia and where the $CO_2$ content of the gas exceeds 45 mol percent. The invention is particularly applicable to carbon dioxide flooding projects for enhanced oil recovery or the processing of hydrocarbon gas streams naturally containing the high percentages of $CO_2$.

In $CO_2$ flooding projects for enhanced oil recovery, $CO_2$ is injected into the formation at a typical pressure range of 1,000–3,000 psia. The affect of the pressure along with the miscibility of $CO_2$ in the oil in the reservoir result in the additional production of oil. Usually about 6,000–18,000 SCF of $CO_2$ are required for recovery of one barrel of oil.

For an initial period of time, there is little or no $CO_2$ exiting the wellhead with the oil. However, after this $CO_2$ breakthrough period which may commonly occur six months to thirty months after the initiation of the flood, about 50–80% of the injected $CO_2$ breaks through the reservoir and exits the wellhead at low pressure, along with hydrocarbon products. The balance of the $CO_2$ dissipates in the formation and is not recoverable. Recovery of the wellhead $CO_2$ and the associated light hydrocarbons is an essential factor to make the enhanced oil recovery by $CO_2$ flood an economical operation. A typical gas composition after this $CO_2$ breakthrough may be commonly in the following range:

| Component | Mol % |
| --- | --- |
| $CO_2$ | 60–90 |
| $H_2S$ | 0–3 |
| $CH_4$ | 5–15 |
| $C_2H_6$ | 3–10 |
| $C_3$-$H_8$ | 2–6 |
| $C_4^+$ | 2–5 |
| $N_2$ | 0–2 |

After the breakthrough, the $CO_2$ content may increase gradually with time and the hydrocarbon content may decrease at a moderate rate as the reservoir is depleted. When the reservoir is abandoned (say, after approximately ten years), the $CO_2$ content in the wellhead gas may exceed 90%.

The separation of the $CO_2$ is required since the $CO_2$ is a valuable fluid for reinjection into the reservoir, thus reducing the $CO_2$ makeup rate. Also, the separation produces valuable sales gas and liquid hydrocarbons products.

The specifications for the reinjected $CO_2$ are a function of the reservoir characteristics, but a common specification range may be as follows:

| | |
| --- | --- |
| 1. $CO_2$ injection pressure: | 1,000–3,000 psia |
| 2. $CO_2$ purity: | >95% |
| 3. $H_2S$ content: | <100 ppm |

Usually higher $CO_2$ purity results in higher yield of liquid and gas products. For example, typical specifications for a sales gas are:

| | |
| --- | --- |
| 1. Methane content: | >90% |
| 2. $CO_2$ content: | <5% |
| 3. Sulfur ($H_2S$, $CS_2$, COS): | <4 ppm |
| 4. Pressure: | 500–1,200 psia |
| 5. Higher heat valve: | >950/Btu/scf |

There are several major prior art approaches for the separation recoveries of $CO_2$ and hydrocarbons. One is the amine or other alkaline scrubbing of $CO_2$ at 100–400 psia (total pressure) and a combination of pressure and temperature swing for the regeneration of the $CO_2$. This system requires relatively high heat energy for the chemical breakdown to regenerate the $CO_2$ and energy to recompress the $CO_2$ to reinjection pressure. Another system is membrane separation at pressures of 300–1,000 psia where the bulk of the $CO_2$ containing small but still undesirable portions of hydrocarbons are recovered as permeate at pressures of about 30–100 psia and then recompressed for reinjection. There is a large pressure drop and thus high energy for multistage recompression.

A third system is the use of a physical solvent such as Selexol where $CO_2$ and $H_2S$ along with some hydrocarbons are absorbed at pressure of 200–800 psia. A portion of the $CO_2$ can be recovered at pressure of about 50–100 psia while the balance of it is recovered at atmospheric pressure. The $CO_2$ is then recompressed to the injection pressure which again requires considerable energy. Also, the fact that some of the hydrocarbons and particularly the $C_{2+}$ are absorbed in the physical solvent is a drawback. Another system is cryogenic distillation where a liquid $CO_2$ is separated from hydrocarbons at a pressure range of 250–450 psia where $H_2S$ is either absorbed upstream selectively to $CO_2$ by amine solution (such as M.D.E.A.) or cryogenically separated along with the $C_{3+}$ products.

One of the potential obstacles which may be encountered in the fractionation of $CO_2$ and hydrocarbons is $CO_2$ freezing occuring at about $-70°$ F. This freezing could occur in the $CH_4$—$CO_2$ separation column. The second obstacle is the $CO_2/C_2H_6$ azeotrope formation at about 70 mol % $CO_2$ and 30 mol % $C_2H_6$ for a binary system, which makes it difficult to separate $C_2H_6$ from $CO_2$. These problems have been solved in the past by injection of $C_{4+}$ and LPG into the feed gas or the fractionation tower. The $C_{4+}$ increases the relative volatility of $CO_2$ over $C_2H_6$. The $C_{4+}$ also suppresses $CO_2$ freezing, thus allowing $CO_2$—$CH_4$ fractionation at low temperatures.

The concept of using $CO_2$ absorption with water has been used in the past for scrubbing $CO_2$ from ammonia synthesis gas; however, the $CO_2$ in that application was a low pressure (under 30 psia) waste product which was merely vented to the atmosphere, its concentration was under 35 mol % and the bulk of the gas was CO, $H_2$ and $N_2$ rather than $CH_4$ and $C_2H_6$ as in the present invention. The co-absorption of $CO_2$ and $H_2S$ by water in natural gas treating has also been done in the past. However, the co-absorbed $CO_2$ was flashed along with the $H_2S$ at low pressure (under 30 psia) only as a sulfur plant feed gas. There was no separation of $CO_2$ from $H_2S$ or any other attempt to recover $CO_2$.

Another approach which has been proposed for $CO_2$—$C_2H_6$ separation is carried out by a membrane which is preceded by a cryogenic demethanizer using the $C_{4+}$ recycle mentioned above. The $CO_2$ permeate has to be recompressed by a multistage compressor to the well injection pressure.

An approach which uses liquid $CO_2$ extraction by liquid water (total liquid phase), where $CO_2$ is separated from ethane has been proposed in copending Patent Application Ser. No. 583,467, filed Feb. 24, 1984.

SUMMARY OF THE INVENTION

The present invention relates to the separation of $CO_2$ from $H_2S$, $CH_4$, $C_2H_6$ and other light hydrocarbons resulting from $CO_2$ flood enhanced oil recovery. More specifically, the separation is by water absorption at high pressure, thus avoiding the $CO_2$—$C_2H_6$ azeotrope problem and providing the $CO_2$ at a pressure of 550–800 psia ready for easy liquefaction, (at about 40°–60° F.), or single stage recompression to the well injection pressure.

BRIEF DESCRIPTION OF THE DRAWING

The drawing is a flow diagram of the present invention.

DESCRIPTION OF THE PREFERRED EMBODIMENT

The gas mixture from the well containing the $CO_2$ and light hydrocarbons as well as $H_2S$ is delivered at about 250–400 psia and then undergoes dehydration by conventional drying systems such as triethylene glycol or molecular sieves (not shown). The following composition and process conditions for the feed gas 10 in the drawing have been used herein to illustrate the invention and to generate a consistent heat and material balance:

TABLE I

| Composition | Mol % |
|---|---|
| $CO_2$ | 70.16 |
| $H_2S$ | 1.20 |
| $CH_4$ | 12.22 |
| $C_2H_6$ | 6.71 |
| $C_3H_8$ | 5.23 |
| $iC_4$ | 1.07 |
| $nC_4$ | 2.09 |
| $iC_5$ | 0.49 |
| $nC_5$ | 0.27 |
| $C_6^+$ | 0.12 |
| $N_2$ | 0.44 |
| Flow Rate: | 50 MMSCFD |
| Pressure: | 335 psia |
| Temperature, °F.: | 105 |
| Total Gas Flow: | 5,590 lb. mol/hr |

The feed gas 10 is introduced into the distillation column indicated at 12. The overhead 13 from the column 12 at −2° F. undergoes condensing at 14 and is then separated into vapor 16 and liquid at 15. The liquid from 15 becomes the reflux to column 12. The bottom from column 12 at about 30° F. is heated at reboiler 17 to about 50° F. where product $CO_2$ is liquified, and then fed to trim reboiler 18 where the bottom product is raised to a temperature of about 105° F. The bottom product 19 is withdrawn from the reboiler. Essentially all the $CH_4+$, 96–98% of the $CO_2$ and about 95% of the $C_2H_6$ will be recovered in the overhead vapor product 16. About 5% of the $C_2H_6$ and about 99% of all the $H_2S$ and essentially all the $C_3+$ are separated as the liquid bottom product 19. The criteria for the $CO_2$—$H_2S$ separation is a limit of 100 ppm $H_2S$ imposed on the $CO_2$ product downstream. Considering the specific feed gas composition given above, the yield from the distillation system 12 is as follows:

TABLE II

| Composition | Top Product (16) Lb. Mol/Hr | Bottom Product (19) Lb. Mol/Hr |
|---|---|---|
| $CO_2$ | 3,751.3 | 100.15 |
| $H_2S$ | 0.395 | 65.46 |
| $CH_4$ | 670.9 | Trace |
| $C_2H_6$ | 352.50 | 15.88 |
| $C_3H_8$ | 0.48 | 287.00 |
| $iC_4$ | Trace | 58.73 |
| $nC_4$ | Trace | 114.71 |
| $C_5$ | Trace | 41.71 |
| $C_6^+$ | Trace | 6.586 |
| $N_2$ | 24.16 | Trace |
| Total | 4,799.73 | 690.226 |
| Temperature | −9° F. | +105° F. |

The bottom product 19 from the fractionation system 12 is routed to a standard sour liquids processing where sulfur is removed and the various liquid components may be separated as desired. The overhead vapor product 16 from the fractionation system 12 will be at a pressure of about 325 psia and −9° F. For the purposes of the present invention, this overhead vapor product 16 contains at least 45 mol % $CO_2$ and less than 0.2 mol % $H_2S$. This vapor product is compressed to 860 psia in the compressor 20. The invention is applicable to pressures above 500 psia. This compressed gas at 143° F., is then cooled at 21 by air or cooling water to the lowest feasible temperature of about 95°–120° F. at summer conditions. This cooled gas is then fed to the bulk $CO_2$ absorption system 22. The $CO_2$ gas is absorbed by a lean solution 24 of $CO_2$ in water at about 850 psia and 95°–100° F. The lower water temperature will enhance $CO_2$ absorption and it is determined by the practical limits of using cooling water. About 90–95% of the $CO_2$ is absorbed by the lean water solution which contains about 1 wt. % residual $CO_2$. The absorber bottom 26 consists of a $CO_2$ solution of about 3.5 wt. % $CO_2$ and about 100 (molar) ppms $CH_4+C_2H_6$. The absorber overhead products 28 are as follows:

TABLE III

| Composition | Vapor Product 28 Lb. Mol/Hr |
|---|---|
| $CO_2$ | 203.7 |
| $H_2S$ | 0.0166 |
| $CH_4$ | 660.6 |
| $C_2H_6$ | 349.0 |
| $C_3H_8$ | 0.048 |
| $C_4^+$ | Trace |
| $N_2$ | 24.13 |
| Total | 1,240.8 |

The overhead gas 28 from the absorption system 22 is fed to a selected conventional process such as amine or Benfield process for gas purification and residual $CO_2$ recovery (not shown).

A large portion of the bottom product 26 from the water absorption system containing about 3.5 wt. % $CO_2$ at about 100° F. is let down through hydraulic turbine 30 to about 350 psi and mechanical power is recovered, and about 55% of the $CO_2$ is flashed at 32. A portion of the remaining solution (about 80%) is recycled to unit 22 through pump 33 as a semi-lean solution 34. The remainder of the solution 36 from flask tank 32 is then heated at 38° to about 210° F., utilizing heat recovery from the lean solution. The final heating from 210°-220° F. to 230°-240° F. is done at 40 by using 50 psig steam hot oil system or any low level heat source such as gas turbine exhaust gas or compressor discharge gas. The liquid is then flashed at 42. At the temperature range of 230°-240° F., the $CO_2$ concentration in the solution is reduced to about 20-25% of the original rich solution at 100° F. The lean solution 24 at 230°-240° F. is cooled at 38 to about 110° F. by preheating the rich solvent as described before. The lean solution at 110° F. is further cooled at 44 by cooling water to the lowest feasible temperature, which is about 10°-15° F. above inlet water temperature and in this illustration is about 95° F. for summer conditions. A refrigerated system can also be used where the solution temperature will be brought to about 75°-80° F. using conventional combination of air cooling, water cooling and propane refrigeration. If the heat is very valuable, than an alternate way of generating lean solution is by further flashing a part of the solution (about 15-30%) through the power recovery turbine 53 into the flash tank 54 to pressure of about 150 psia. The lean solution from 54 is recycled by pump 55 to the absorption system 22. In this situation, compression energy at 56 will be traded against heating energy at 40. An absorption temperature of 60°-80° F. would be suitable for such a scheme.

The $CO_2$ which is regenerated at 42 is cooled at 46 and combined with the $CO_2$ from the top of flash tank 32 and the $CO_2$ from compressor 56 to form the combined $CO_2$ stream 47. This combined $CO_2$ stream 47 is then compressed to about 850 psi by compressor 48. $CO_2$ at 850 psia is liquified at 17 by providing part of the reboiling duty for fractionation 12 or for side reboiling (not shown). Liquid $CO_2$ may be pumped to the desired pressure at 50.

A modification of the invention involves an alternative scheme for removing residual $H_2S$ from the $CO_2$ by a destructive oxidation process. The $H_2S$ content of the overhead 16 from column 12 is increased from a level of 80 ppm to about 800 ppm. This will reduce the size and refrigeration consumption of unit 12 by 30 to 40%. The combined $CO_2$ stream 47 at 350 psia with about 1000 ppm $H_2S$ undergoes catalytic oxidation by the injection of air into unit 52. Conventional processes can be used where over 90% of the $H_2S$ is converted to elemental sulfur while only small amounts of nitrogen (about 0.2%) are added to the $CO_2$ product.

A further feature or modification of the invention is that the water used for $CO_2$ absorption in column 22 may be a mixture of water and a water soluble organic additive with a low affinity for ethane an a high affinity for $CO_2$ such as methanol or propylene carbonate or a combination of both. In such a case, the methanol or propylene carbonate will remain in the water phase. The solubility of $CO_2$ in methanol is several times as great as the solubility in water. However, ethane is also somewhat soluble in methanol. Therefore, up to 35 mol % methanol or 10 mol % propylene carbonate may be used which will significantly increase the solubility of the carbon dioxide but will not greatly increase the ethane loss. For example, using 20 mol % methanol in the water (without propylene carbonate) may increase $CO_2$ solubility by about 40%. While the hydrocarbon solubility will also increase, this increase may be on the order of from 200 (mol) to 600 (mol) ppm which still amounts to a low hydrocarbon loss. The effect of the use of this mixture of water and methanol is that the circulation rate of the water phase through the extraction column may be 70-80% or less of what it would otherwise be.

We claim:

1. A process for the separation and recovery of $CO_2$ from an enhanced oil recovery or naturally occurring gas stream containing a mixture of at least 45 mol % $CO_2$ and less than 0.2 mol % $H_2S$ with light hydrocarbons containing ethane as a primary light hydrocarbon component comprising the steps of:
   (a) providing a gas stream of said mixture at a pressure of at least 500 psia,
   (b) introducing said gas stream into the lower portion of an absorption system,
   (c.) introducing a first liquid water phase containing at least 65 mol % water and containing less than about 1.4 weight % $CO_2$ into the top portion of said absorption system and a second liquid water phase containing at least 65 mol % water and containing between about 1.4 and 3.0 weight % $CO_2$ into the middle portion of said absorption system to form a downwardly flowing liquid water phase whereby said gas stream flows upwardly in contact with said downwardly flowing liquid water phase and said downwardly flowing liquid water phase absorbs $CO_2$ from said gas stream to form a $CO_2$-rich liquid water phase,
   (d.) withdrawing said gas stream depleted in $CO_2$ from the top portion of said absorption system,
   (e.) withdrawing said $CO_2$-rich liquid water phase from the bottom portion of said absorption system at a pressure of at least 500 psia,
   (f.) separating gaseous $CO_2$ from said withdrawn $CO_2$-rich liquid water phase to form said recovered $CO_2$ and said first liquid water phase containing less than 1.4 mol % $CO_2$ and said second liquid water phase containing between about 1.4 and 3.0 weight % $CO_2$, and
   (g.) recycling said separated first and second liquid water phases to the top and middle portions of said absorption system respectively.

2. The process of claim 1 wherein said separating step (e) comprises reducing the pressure of said withdrawn $CO_2$-rich liquid water phase and flashing said $CO_2$ at a pressure of at least 100 psia therefrom.

3. The process of claim 2 wherein said separating step (e) further includes the step of heating said withdrawn $CO_2$-rich liquid water phase and further flashing said $CO_2$ therefrom.

4. The process of claim 3 wherein said heating at least partially comprises transferring heat from said separated first liquid water phase to said withdrawn $CO_2$-rich liquid water phase.

5. The process of claim 1 wherein said separating step (e) further comprises additional pressure reduction and flashing steps.

6. A process as recited in claim 1 wherein said gas stream also contains less than 0.2% $H_2S$, said $H_2S$ being withdrawn with said $CO_2$-rich liquid water phase from the bottom of said absorption system and being separated with said gaseous $CO_2$ and further including the steps of oxidizing said $H_2S$ in said gaseous $CO_2$ stream to elemental sulfur and removing said elemental sulfur.

7. The process of claim 1 wherein said step (a) of providing a gas stream comprises the step of fractionating a feed gas stream containing said $CO_2$ and said ethane and further containing heavier hydrocarbons and $H_2S$ into an overhead product containing primarily said $CO_2$ and said ethane and a bottom product containing primarily said said heavier hydrocarbons and $H_2S$ and further including the step of transferring heat from said recovered $CO_2$ to said bottom product from said fractionation to liquify said recovered $CO_2$.

* * * * *